United States Patent [19]

Redl

[11] 4,125,610
[45] Nov. 14, 1978

[54] ANTIBACTERIAL COMPOSITIONS

[75] Inventor: George Redl, Williamsville, N.Y.

[73] Assignee: Bristol-Myers Company, New York, N.Y.

[21] Appl. No.: 819,523

[22] Filed: Jul. 27, 1977

[51] Int. Cl.² .................... A61K 31/66; A61K 31/505
[52] U.S. Cl. ..................................... 424/211; 424/251
[58] Field of Search ............................. 424/251, 211

[56] References Cited

U.S. PATENT DOCUMENTS

| 3,159,573 | 12/1964 | Takesue et al. | 424/211 |
| 3,852,450 | 12/1974 | Silvestri et al. | 424/251 |

OTHER PUBLICATIONS

Antibiotics and Chemotherapy, 3, pp. 256–264 (1953).

Primary Examiner—Jerome D. Goldberg
Attorney, Agent, or Firm—Richard R. Lloyd

[57] ABSTRACT

Oral antibacterial compositions comprising mixtures of phosphanilic acid and trimethoprim are described.

9 Claims, 4 Drawing Figures

SYNERGISTIC ACTIVITY OF PHOSPHANILIC ACID IN COMBINATION WITH TRIMETHOPRIM

SYNERGISTIC ACTIVITY OF PHOSPHANILIC ACID IN COMBINATION WITH TRIMETHOPRIM

SYNERGISTIC ACTIVITY OF PHOSPHANILIC ACID IN COMBINATION WITH TRIMETHOPRIM

ANTIBACTERIAL COMPOSITIONS

SUMMARY OF THE INVENTION

Compositions comprising mixtures of phosphanilic acid and trimethoprim are orally effective antibacterial agents which exhibit synergistic activity against various microorganisms, including *Pseudomonas aeruginosa.*

BACKGROUND OF THE INVENTION

Phosphanilic acid [p-aminophenylphosphonic acid] has been reported in the literature as having antibacterial activity against various microorganisms. It has now been found that mixtures of phosphanilic acid and trimethoprim [2,4-diamino-5-(3',4',5'-trimethoxybenzyl)pyrimidine] in ratios of from about 0.25:1 to about 20:1 exhibit surprisingly high synergistic activity against many strains of bacteria.

DESCRIPTION OF THE PRIOR ART

Trimethoprim is a known compound, having been disclosed and claimed per se in U.S. Pat. No. 2,909,522. It and related compounds are stated therein to be useful in the treatment of bacterial and protozoal disease. The patent also discloses that the compounds potentiate sulfonamides and that they are useful as a topical bacterial agent in combination with polymixin.

U.S. Pat. No. 3,515,783 and its reissue Re 28,636 disclose that a mixture of 5-methyl-3-sulfanilamidopyrimidine, or a pharmaceutically acceptable salt thereof, with trimethoprim is an orally active antibacterial agent, particularly against a sulfonamide-resistant strain of *Proteus vulgaris.*

U.S. Pat. No. 3,985,876 discloses combinations of substituted 2,4-diaminopyrimidines (including trimethoprim) with sulfonamides such as sulfadimethoxine, sulfadiazine, sulfadoxine, sulfamethoxazol, sulfaquinoxaline, sulfadimidine, sulfafurazole and sulfacetamide. They are clear solutions for oral or parenteral use prepared by mixing an aqueous solution of a pharmaceutically acid salt of the substituted 2,4-diaminopyrimidine with a pharmaceutically acceptable water-miscible organic solvent solution of the sulfonamide.

Various other patents disclose combinations of substituted 2,4-diaminopyrimidines (including trimethoprim) with particular sulfonamides, e.g. U. K. Pat. No. 1,372,981 (Farmdoc 77973V) disclosing the mixture with 2-sulfanilamido-4,5-dimethyloxazole which is stated to be active against plasmodia and useful for treating malaria; U.S. Pat. No. 3,996,356 disclosing the mixture with 5-sulfanilamido-3,4-dimethylisoxazole which is stated to be active against strains resistant to the sulfonamide; U.S. Pat. No. 3,996,357 disclosing the mixture with N-sulfanilyl-1-ethylcytosine which is stated to be particularly useful for urinary tract infections.

Belgian Pat. No. 825,496 (Farmdoc 44444W) and its Patent of Addition 838,506 (Farmdoc 52127X) disclose tablets containing trimethoprim, a sulfonamide such as sulfamethoxaxole, a granulating agent and a disintegrating agent having a swelling capacity of more than 5 ml.g/. The tablets are stated to be smaller than prior art tablets but with good hardness and disintegration times.

Combinations of trimethoprim and other antibacterial agents also are known. Thus, Belgian Pat. No. 829,199 (Farmdoc 80246W) discloses a mixture of trimethoprim and 6-(homopiperidinomethyleneimino)penicillanic acid or an ester thereof, having the formula

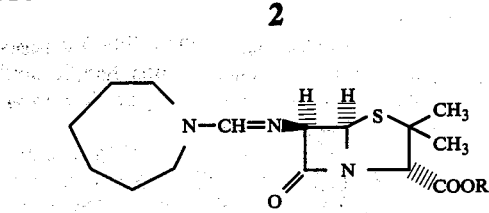

in which R is hydrogen or (lower)alkanoyloxymethyl. The mixture is stated to have a strong synergistic effect against Gram-negative bacteria such as *E. coli, Salmonella, Haemophilus* and *Proteus* species.

West German Pat. No. 2,402,200 (Farmdoc 55570V) discloses a mixture of trimethoprim and erythromycylamine which is stated to be active against various Gram-positive and Gram-negative bacteria.

U.S. Pat. No. 3,852,450 discloses a mixture of trimethoprim and rifampicin which is stated to show synergism against various bacteria.

U.S. Pat. No. 3,574,833 discloses that a mixture of trimethoprim and sulfalene is useful in the treatment of malaria, particularly the drug-resistant *P. falciparium* strain of malaria.

West German Pat. No. 2,404,594 (Farmdoc 60246V) discloses mixtures of pyrimidine derivatives such as trimethoprim with 2-amino-4-hydroxy-7,8-dihydropteridines of the formula

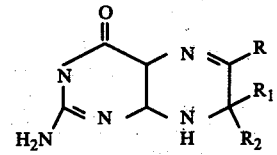

wherein (a) R is substituted phenoxyalkyl or formyl and $R_1$ and $R_2$ are (lower)alkyl or together form a spiroalkyl ring having 4–6 carbon atoms, (b) R is chloromethyl and $R_1$ and $R_2$ are methyl, or (c) R is 1-bromoethyl and $R_1$ and $R_2$ are n-propyl. These combinations are stated to be synergistic against various bacteria and protozoa which produce at least part of their own tetrahydrofolate cofactor, e.g. *Staph. aureus, Pseudomonas aeruginosa* and *Pasteurella multocida.*

Chemical Abstracts, 77, 160523r (1972), citing Int. J. Clin. Pharmacol., Ther. Toxicol,. 6, 285–290 (1972), discloses that a mixture of trimethoprim and colistin shows synergistic activity in agar diffusion tests against 99 of 100 Proteus strains resistant to colistin alone.

Chemical Abstracts, 77, 14802q (1972), citing An. Inst. Farmacol. Espan. 19, 341–350 (1970) [published 1971], discloses synergistic mixtures of phosphonomycin of the formula

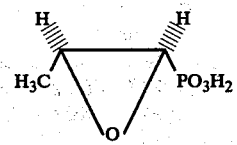

with ampicillin, trimethoprim, gentamycin, chloramphenicol, erythromycin or kanamycin. The mixtures of phosphonomycin and trimethoprim (each at 0.125–0.256 mcg./ml.) showed synergism in 70–80% of the cases in agar plate tests with bacterial clinical isolates.

Current Science (India), 16, 223-225 (1947) reports the in vitro antibacterial activity of phosphanilic acid and some of its derivatives against *E. coli, S. aureus, Typhi murium, C. xerosis* and Boyd II.

Current Science (India), 17, 125-6 (1948) reports blood level and toxicity studies with phosphanilic acid in laboratory animals. Their results indicated poor absorption and low toxicity.

J. Pharmacol. Exp. Therap., 74, 163-173 (1942) reports the testing of various sulfonamides, sulfones and related phosphorus compounds against experimental tuberculosis. They found that phosphanilic acid had good tubercularstatic activity in vitro but no effect in vivo, presumably due to low blood concentrations of phosphanilic acid.

Chemical Abstracts, 55, 2883 g (1961) [from Texas Repts. Biol. and Med., 18, 379-394 (1960)] reports that phosphanilic acid had some protective effect when tested in white mice against a standardized infection produced by intravenous injection of the yeast phase of *Histoplasma capsulatum*.

Antibiotics and Chemotherapy, 3, 256-264 (1953) report the in vitro activity of some aromatic phosphonic and phosphinic acids against a variety of bacterial species. Phosphanilic acid was reported as being generally the most active of the compounds tested. Its activity approached that of sulfathiazole when compared on a molar basis and its antibacterial spectrum was similar to that of sulfanilamide. It was also stated that a later paper would report in detail the findings that phosphanilic acid was effective in vivo in mice infected with *S. typhosa, Ps. fluorescens* and *Plasmodium berghei*.

U.S. Pat. No. 3,159,537 discloses the potentiation of various tetracycline antibiotics by admixture with (or salt formation with) various organic oxyphosphorous compounds, including phosphanilic acid.

Ciencia (Mexico), 17, 71-73 (1957) reports studies of the in vitro synergism of mixtures of phosphanilic acid with neomycin or streptomycin on various clinically isolated strains of Salmonella, Shigella and Proteus as well as coliform bacteria capable of inducing fermentation of lactose. The combination of phosphanilic acid and neomycin showed synergism against Salmonella, Proteus and the coliform bacteria. With Shigella, however, there was only slight synergism for low concentrations and only an additive effect, or no effect, at medium and high concentrations.

DETAILED DESCRIPTION

In its most comprehensive embodiment the present invention relates to an orally active antibacterial composition comprising from about 0.25 to about 20 parts of phosphanilic acid or a pharmaceutically acceptable salt thereof and one part of trimethoprim or a pharmaceutically acceptable salt thereof, preferably in combination with a pharmaceutically acceptable carrier.

In a preferred embodiment, the composition comprises from about 2 to about 7 parts (and most preferably about 5 parts) of phosphanilic acid or a pharmaceutically acceptable salt thereof and one part of trimethoprim or a pharmaceutically acceptable salt thereof.

In another aspect, this invention relates to an antibacterial composition for oral administration in shaped dosage unit form comprising from about 100 to about 1600 milligrams of phosphanilic acid or a pharmaceutically acceptable salt thereof and from about 20 to about 320 milligrams of trimethoprim or a pharmaceutically acceptable salt thereof.

In a preferred embodiment the shaped dosage unit form comprises from about 400 to about 800 milligrams of phosphanilic acid or a pharmaceutically acceptable salt thereof and from about 80 to about 160 milligrams of trimethoprim or a pharmaceutically acceptable salt thereof.

In still another aspect, this invention relates to a method of treating a warm-blooded animal afflicted with a bacterial disease which comprises orally administering to said warm-blooded animal a therapeutically effective amount of a composition comprising from about 0.25 to about 20 parts of phosphanilic acid or a pharmaceutically acceptable salt thereof and one part of trimethoprim or a pharmaceutically acceptable salt thereof.

In a preferred embodiment of the method, the therapeutically effective amount of the composition comprises from about 100 to about 160 milligrams of phosphanilic acid or a pharmaceutically acceptable salt thereof and from about 20 to about 320 milligrams of trimethoprim or a pharmaceutically acceptable salt thereof.

In a more preferred embodiment of the method, the therapeutically effective amount of the composition comprises from about 400 to about 800 milligrams of phosphanilic acid or a pharmaceutically acceptable salt thereof and from about 80 to about 160 milligrams of trimethoprim or a pharmaceutically acceptable salt thereof.

The term pharmaceutically acceptable salts used throughout the specification and claims in connection with trimethoprim denotes salts formed using pharmaceutically acceptable inorganic or organic acids such as hydrochloric, sulfuric, acetic, citric, lactic, maleic and the like.

Phosphanilic acid contains both acidic and basic groups and thus can form salts with bases or acids. It preferably is utilized in its free form in the compositions of this invention but, if desired, may be utilized as a salt of an acid such as described above or a salt of a base such as sodium hydroxide, potassium hydroxide and the like. The term pharmaceutically acceptable salt used throughout the specification and claims in connection with phosphanilic acid is intended to include both acidic and basic salts.

The compositions of this invention are prepared simply by admixing the desired amounts of phosphanilic acid, or a pharmaceutically acceptable salt thereof, and trimethoprim or a pharmaceutically acceptable salt thereof. The ratio in which the two active ingredients are utilized in the compositions of this invention may be varied within rather wide limits. As seen in Table 2, synergism may be demonstrated with either active ingredient in excess, and the choice depends on various factors, including the particular microorganism involved. It is usually preferred that the compositions contain a 5:1 ratio of phosphanilic acid: trimethoprim. Preferred unit dosage forms are those containing about 400 mg of phosphanilic acid and about 80 mg of trimethoprim and a double strength dosage form containing about 800 mg of phosphanilic acid and about 160 mg of trimethoprim. A typical dosage regimen is one such double strength dosage unit (or 2-3 single strength dosage units) every twelve hours. The foregoing notwithstanding, it should be fully understood that the ratios or amounts of active ingredients and the dosages set forth herein are exemplary only, and they do not, to any extent, limit the scope of the present invention.

Throughout the specification and claims reference is made to the use of specified amounts, e.g. 400 mg, of "phosphanilic acid or a pharmaceutically acceptable salt thereof" as well as specified amounts, e.g. 80 mg, of "trimethoprim or a pharmaceutically acceptable salt thereof." Such language is intended to mean the specified amount of the particular ingredient or the equivalent amount of a pharmaceutically acceptable salt thereof. Thus, for example, in place of 80 mg of trimethoprim, one would utilize 90 mg of trimethoprim monohydrochloride.

The mixture is ultimately embodied into a suitable oral dosage form. For example, the compositions of this invention can be compressed by usual methods into single or multi-layer tablets. Moreover, they can be produced in the form of coated tablets or provided in the form of hard-shell capsules. They are also useful as oral suspensions or powders for reconstitution into oral suspensions. In general, the various oral dosage forms of the present compositions are prepared by the conventional procedures and techniques of the art. The applicability of such methods and techniques to the formulation of the compositions of the present invention will be readily apparent to those skilled in the art.

In addition to the therapeutically active ingredients mentioned heretofore, the compositions of this invention can contain as optional ingredients any of the various adjuvants which are used ordinarily in the production of pharmaceutical preparations. Thus, for example, in formulating the present compositions into the desired oral dosage forms, one may use as optional ingredients any of the usual fillers, disintegrating agents or lubricating agents, e.g. lactose, gum arabic, starch, talc, magnesium or calcium stearate, gelatin, and the like. It should be fully understood, however, that the optional ingredients herein named are given by way of example only and that the invention is not restricted to the use thereof. On the contrary, other adjuvants such as preservatives, stabilizers, suspending agents or buffers, the identity and use of which are well known in the art, can be, and are, employed in carrying out this invention.

The Minimum Inhibitory Concentrations (MIC's) of phosphanilic acid and trimethoprim alone and in 1:1, 2.5:1 and 5:1 mixtures were determined against a number of microorganisms, and the results are shown in Table 1.

Table 1

Antibacterial Activity of Phosphanilic Acid (P) and Trimethoprim (T) Alone and in Combinations

| Organism | | P | T | P:T 1:1 | P:T 2.5:1 | P:T 5:1 |
|---|---|---|---|---|---|---|
| Staph. aureus | A-9537 | >125 | 0.25 | 0.5 | 1 | 1 |
| Staph. aureus | A-9606 | >125 | 0.25 | 0.5 | 1 | 1 |
| Staph. aureus | A15097 | >125 | 0.25 | 0.5 | 1 | 1 |
| E. coli | A-9675 | >125 | .06 | 0.13 | 0.5 | 0.5 |
| E. coli | A-9671 | >125 | 0.13 | 0.13 | 0.5 | 0.5 |
| E. coli | A15119 | >125 | 0.5 | 0.13 | 0.5 | 0.5 |
| Kl. pneumoniae | A-9977 | >125 | 0.25 | 0.13 | 0.5 | 0.5 |
| Kl. pneumoniae | A15130 | >125 | 0.5 | 1 | 2 | 4 |
| Kl. pneumoniae | A20468 | >125 | 8 | 8 | 8 | 8 |
| Pr. mirabilis | A-9900 | >125 | 2 | 0.25 | 1 | 1 |
| Pr. mirabilis | A-9696 | >125 | 4 | 0.5 | 1 | 1 |
| | A20119 | >125 | 16 | 1 | 2 | 2 |
| Ent. cloacae | A-9656 | >125 | 4 | 2 | 4 | 4 |
| Ent. cloacae | A-9657 | 63 | .06 | 0.13 | 0.25 | 0.25 |
| Ent. cloacae | A-9659 | >125 | 0.25 | 0.5 | 1 | 1 |
| Ps. aeruginosa | A-9843a | 4 | >125 | 4 | 4 | 4 |
| Ps. aeruginosa | A-9925 | 16 | 125 | 8 | 4 | 4 |
| Ps. aeruginosa | A20229 | 63 | 125 | 8 | 16 | 16 |
| Ps. aeruginosa | A20543 | 16 | 32 | 8 | 8 | 8 |
| Ps. aeruginosa | A20126 | 16 | 125 | 8 | 16 | 16 |
| Ps. aeruginosa | A15151 | 1 | 63 | 1 | 1 | 1 |
| Ps. aeruginosa | A20227 | 1 | 32 | 0.5 | 0.5 | 0.5 |
| Ps. aeruginosa | A20574 | 1 | 125 | 1 | 1 | 1 |
| Ps. aeruginosa | A20602 | 125 | 125 | 16 | 16 | 63 |

*The MIC's were determined by the twofold broth dilution method following overnight incubation at 37° C in Meuller-Hinton Broth containing 2% lysed defibrinated horse blood and using $10^{-4}$ dilutions of overnight broth cultures ($10^{-3}$ dilutions of Staph. aureus strains A9606 and A15097) as inocula at the rate of 0.5 ml of inoculum per 0.5 ml of medicated broth.

In a more extensive series of tests, the geometric mean MIC's of phosphanilic acid and trimethoprim alone and in mixtures of from 0.25:1 to 16:1 were determined against a wider variety of microorganisms. The geometric mean MIC's were determined from MIC's obtained in two separate tests of each of the strains of Staphylococcus and Proteus, and three separate tests for each of the other organisms.

Table 2

Antibacterial Activity of Trimethoprim (T) and Phosphanilic Acid (P), Alone and in Combinations

| Organism | No. of Strains | P | T | P:T 0.25:1 | P:T 0.5:1 | P:T 1:1 | P:T 2:1 | P:T 4:1 | P:T 8:1 | P:T 16:1 |
|---|---|---|---|---|---|---|---|---|---|---|
| Staph. aureus | 5 | >109 | 0.5 | 0.5 | 0.6 | 0.8 | 1 | 1 | 5.7 | 5.7 |
| E. coli | 1 | 6.4 | 0.1 | 0.1 | 0.1 | 0.1 | 0.1 | 0.3 | 0.5 | 0.6 |
| E. coli | 2 | 18 | 0.3 | 0.3 | 0.3 | 0.4 | 0.3 | 0.6 | 2 | 1.6 |
| E. coli | 2 | >125 | 0.3 | 0.3 | 0.5 | 0.5 | 0.4 | 0.7 | 2 | 3 |
| E. coli | 4 | 20 | 0.4 | 0.4 | 0.4 | 0.5 | 0.5 | 0.8 | 2 | 2 |
| Kl. pneumoniae | 5 | 18 | 0.4 | 0.5 | 0.5 | 0.6 | 0.6 | 0.8 | 1.7 | 2 |
| Kl. pneumoniae | 1 | 40 | 25 | 13 | 13 | 10 | 8 | 10 | 13 | 8 |
| Kl. pneumoniae | 2 | 40 | 0.4 | 0.5 | 0.6 | 0.8 | 0.6 | 1 | 2.2 | 4 |
| Kl. pneumoniae | 1 | >125 | 0.8 | 0.8 | 0.8 | 1 | 2 | 5 | 4 | |
| Ent. cloacae | 1 | 8 | 0.1 | 0.1 | 0.2 | 0.1 | 0.2 | 0.3 | 0.8 | 0.8 |
| Ent. cloacae | 3 | 20 | 0.5 | 0.5 | 0.5 | 0.5 | 0.6 | 0.9 | 1.7 | 2 |
| Ent. cloacae | 1 | >125 | 1 | 1.6 | 3 | 2.5 | 1 | 2.5 | 5 | 6 |
| Ent. cloacae | 2 | 63 | 0.6 | 0.8 | 0.6 | 0.7 | 0.8 | 1 | 2 | 2.5 |
| Pr. mirabilis | 4 | 7.3 | 1.2 | 0.4 | 0.4 | 0.4 | 0.6 | 0.7 | 0.9 | 0.9 |
| Pr. mirabilis | 2 | >105 | 2 | 0.7 | 0.8 | 0.6 | 0.7 | 1.4 | 1.4 | 2.8 |
| Pr. mirabilis | 1 | 11.3 | 2 | 1 | 1 | 0.7 | 0.7 | 1 | 1 | 1.4 |
| Pr. mirabilis | 1 | 16 | 4 | 2 | 4 | 2 | 4 | 16 | 8 | 11.3 |
| Pr. vulgaris | 1 | >125 | 1 | 0.7 | 1 | 1 | 1.4 | 2.8 | 4 | 4 |
| Pr. vulgaris | 2 | 8 | 0.6 | 0.3 | 0.4 | 0.4 | 0.5 | 0.8 | 1 | 0.6 |
| Pr. morganii | 1 | >125 | 28 | 1 | 1 | 1 | 1 | 2 | 2 | 4 |
| Pr. morganii | 2 | 11.3 | 2 | 0.7 | 1.4 | 1 | 1.4 | 0.2 | 1.4 | 0.6 |
| Pr. rettgeri | 1 | 0.5 | 0.7 | 0.2 | 0.5 | 0.1 | 0.4 | 0.4 | 0.4 | 0.5 |
| Pr. rettgeri | 1 | >125 | 5.7 | 8 | 8 | 8 | 16 | 32 | 32 | 45 |

*MIC's determined as described for Table 1, except 5% laked horse blood was utilized.

In interpreting the data presented in Tables 1 and 2 (and Table 4 below), it must be kept in mind that the compositions of the present invention are mixtures and that each of the two active ingredients dilutes the other. Thus, taking as an example the results reported in Table 2 for the first listed strain of Pr. vulgaris, the MIC for phosphanilic acid is >125 μg/ml and the MIC for trimethoprim is 1 μg/ml. The MIC for the 16:1 mixture of phosphanilic acid and trimethoprim is 4 μg/ml which is four times as high, numerically, as the MIC of trimethoprim alone. However, 4 μg/ml of the 16:1 mixture is 3.76 μg/ml of phosphanilic acid (<3.0% of its individual MIC) and 0.235 μg/ml of trimethoprim (23% of its individual MIC). Thus, this mixture demonstrates synergism.

A method of quantitatively evaluating the degree of synergism when two inhibitory substances are used in combination has been described by G. B. Elion, et al., J. Biol. Chem., 208, 477–488 (1954) and K. Mashimo, et al., J. Infect. Dis., 128 Supp., S502–S507 (1973). This method is called the fractional-inhibitory-concentration (FIC) index method, and the FIC index is calculated as shown below:

$$\text{FIC index} = \frac{\text{Fraction of first inhibitor at the MIC in combination}}{\text{MIC of first inhibitor alone}} + \frac{\text{Fraction of second inhibitor at the MIC in combination}}{\text{MIC of second inhibitor alone}}$$

The FIC indices are arbitrarily classified in three grades, as follows:

FIC index ≦ 0.30 indicates strong synergism
FIC index of 0.31–0.60 indicates moderate synergism
FIC index ≧ 0.61 indicates slight or no synergism Using the above illustration of the 16:1 mixture of phosphanilic acid and trimethoprim against the first strain of Pr. vulgaris in Table 2, the FIC index is calculated below:

$$\text{FIC index} = \frac{3.76}{>125} + \frac{.235}{1}$$
$$= <.030 + .235$$
$$= <.265$$

It may be seen that the FIC index indicates strong synergism.

The antibacterial activity of one of the embodiments of this invention, a 5:1 mixture of phosphanilic acid:trimethoprim was compared with a commercially available antibacterial product comprising a 5:1 mixture of sulfamethoxazole:trimethoprim. The tests were run by the agar dilution method using Mueller-Hinton Medium with 5% laked horse blood. A $10^{-3}$ dilution of overnight broth culture was used as inoculum. The MIC's of the commercial product have been corrected for excipients contained therein. Table 3 shows the number of strains of each organism which are inhibited by each of the mixtures at varying concentrations. The commercial product is stated to be active against the common urinary tract pathogens with the exception of Pseudomonas aeruginosa, and this is confirmed by the results shown in Table 3. It may be noted that the composition of this invention exhibited good activity against the strains of Pseudomonas aeruginosa.

Table 3

Antibacterial Activities of 5:1 Mixtures of Phosphanilic Acid (P) or Sulfamethoxazole (S) with Trimethoprim (T)

| Organism Drug Concentration | No. of Strains | Number of Strains Inhibited at Indicated Concentration (μg/ml) | | | | | | | | | | | | |
|---|---|---|---|---|---|---|---|---|---|---|---|---|---|---|
| | | .063 | 0.13 | 0.25 | 0.5 | 1 | 2 | 4 | 8 | 16 | 32 | 63 | 125 | >125 |
| S. aureus | 5 | | | | | | | | | | | | | |
| S/T (5:1) | | | | | | 2 | 3 | 5 | | | | | | |
| P/T (5:1) | | | | | | | | 5 | | | | | | |
| E. coli | 9 | | | | | | | | | | | | | |
| S/T (5:1) | | | | | 2 | 4 | 8 | 9 | | | | | | |
| P/T (5:1) | | | | | | 1 | 9 | | | | | | | |
| K. pneumoniae | 9 | | | | | | | | | | | | | |
| S/T (5:1) | | | | | 1 | 4 | 5 | 7 | 8 | 9 | | | | |
| P/T (5:1) | | | | | | | 2 | 7 | 8 | | 9 | | | |
| E. cloacae | 9 | | | | | | | | | | | | | |
| S/T (5:1) | | | | 1 | | 5 | 6 | 7 | 8 | 9 | | | | |
| P/T (5:1) | | | | | | 1 | 3 | 7 | 9 | | | | | |
| P. mirabilis | 7 | | | | | | | | | | | | | |
| S/T (5:1) | | | | | | 2 | 5 | 6 | 7 | | | | | |
| P/T (5:1) | | | | | 1 | | 5 | 7 | | | | | | |
| Indole + Proteus | 9 | | | | | | | | | | | | | |
| S/T (5:1) | | | | | | 3 | 5 | 6 | 7 | 8 | 9 | | | |
| P/T (5:1) | | | | | 1 | 2 | 4 | 7 | 8 | 9 | | | | |
| P. aeruginosa | 12 | | | | | | | | | | | | | |
| S/T (5:1) | | | | | | | | | | | 4 | 7 | 8 | 12 |
| P/T (5:1) | | 1 | 3 | 4 | | 8 | 10 | 12 | | | | | | |

The isobolograms in FIGS. 1–4 demonstrate the in vitro synergism of mixtures of phosphanilic acid and trimethoprim against various strains of Pr. mirabilis, Pr. vulgaris and Ps. aeruginosa. An isobologram consists of plotting on an arithmetic scale the amounts of drug A and drug B that alone, or in various combinations, produce the same biological effect. The biological effects plotted in FIGS. 1–4 are Minimal Inhibitory Concentrations (MIC's) and Minimal Bactericidal Concentrations (MBC's). In each isobologram, the intercept on the horizontal axis is the MIC or MBC of phosphanilic acid alone against the particular organism, while the intercept on the vertical axis is the MIC or MBC of trimethoprim alone against the same organism. The straight line joining these two points is the plot one would obtain if the effect of the two drugs were merely additive in their various mixtures. If the plot of the actual MIC's or MBC's of various mixtures of the two ingredients bows upward (i.e. is concave downward), the two ingredients are antagonistic in admixture. If the plot of the actual MIC's of various mixtures of the two ingredients bows downward (i.e. is concave upward), the two ingredients are synergistic in admixture. It is to be noted that mixtures of phosphanilic acid and trimethoprim showed strong synergistic activity, for both MIC's and MBC's against each of the organisms.

For these studies, cells from the indicated bacterial strains were exposed to a two-fold series of antibiotic concentrations (singly and in varying combinations) in Mueller-Hinton Broth containing 2% laked horse blood. The inoculum was an overnight culture diluted so as to yield an initial cell concentration of $10^5$–$10^6$ cells/ml. At the termination of a 20–24 hour incubation period at 37° C., readings were made for MIC determinations and the cultures then chilled in ice. Following this, 0.1 ml samples from each turbidity-free tube were plated on solid medium for bactericidal determinations. After incubation of plates for 18–24 hours, colonies were counter to determine the number of viable cells in the original MIC tubes. MBC's were determined on the basis of a 99.9% loss in the number of viable cells.

The Protective Dose$_{50}$ (PD$_{50}$) for phosphanilic acid and trimethoprim alone and in a 5:1 mixture was determined in mice against a number of organisms, and the results are shown in Table 4.

Table 4

Therapeutic Efficacy of Phosphanilic Acid (P), Trimethoprim (T), and Combination of P:T (5:1) after Oral Administration to Mice

| Organism | Challenge (No. of Organisms) | Treatment Schedule (hr Post-Challenge) | PD$_{50}$/treatment (mg/kg) | | |
|---|---|---|---|---|---|
| | | | P | T | P:T (5:1) |
| S. aureus A9537 | $1 \times 10^5$ | 0 and 4 | >100 | 38 | 87 |
| | $3 \times 10^5$ | 0 and 4 | >400 | 100 | 200 |
| S. pyogenes A9604 | 0, 6, 22 and 26 | >400 | >400 | >400 | |
| 0.3–2×10$^4$ | | | | | |
| E. coli A15119 | $1 \times 10^6$ | 0 and 2 | >400 | 262 | 348 |
| | $6 \times 10^5$ | −2, 1, and 3 | >400 | 200 | 200 |
| K. pneumoniae A9977 | $3 \times 10^5$ | 0 and 6 | >400 | — | 151 |
| | $3 \times 10^5$ | 0, 6, 22, 26, 48, and 54 | >400 | 348 | 151 |
| P. mirabilis A9900 | $8 \times 10^6$ | 0 and 2 | >800 | — | 33 |
| | $6 \times 10^6$ | 0 and 2 | >200 | — | 25 |
| | $8 \times 10^6$ | 0 and 2 | >200 | >200 | 25 |
| P. aeruginosa A9843A | $1 \times 10^4$ | 0 and 2 | 4.8$^a$ | — | — |

$^a$In the same experiment, the PD$_{50}$/treatment of carbenicillin, given im., was 77 mg/kg.

Figure 1:
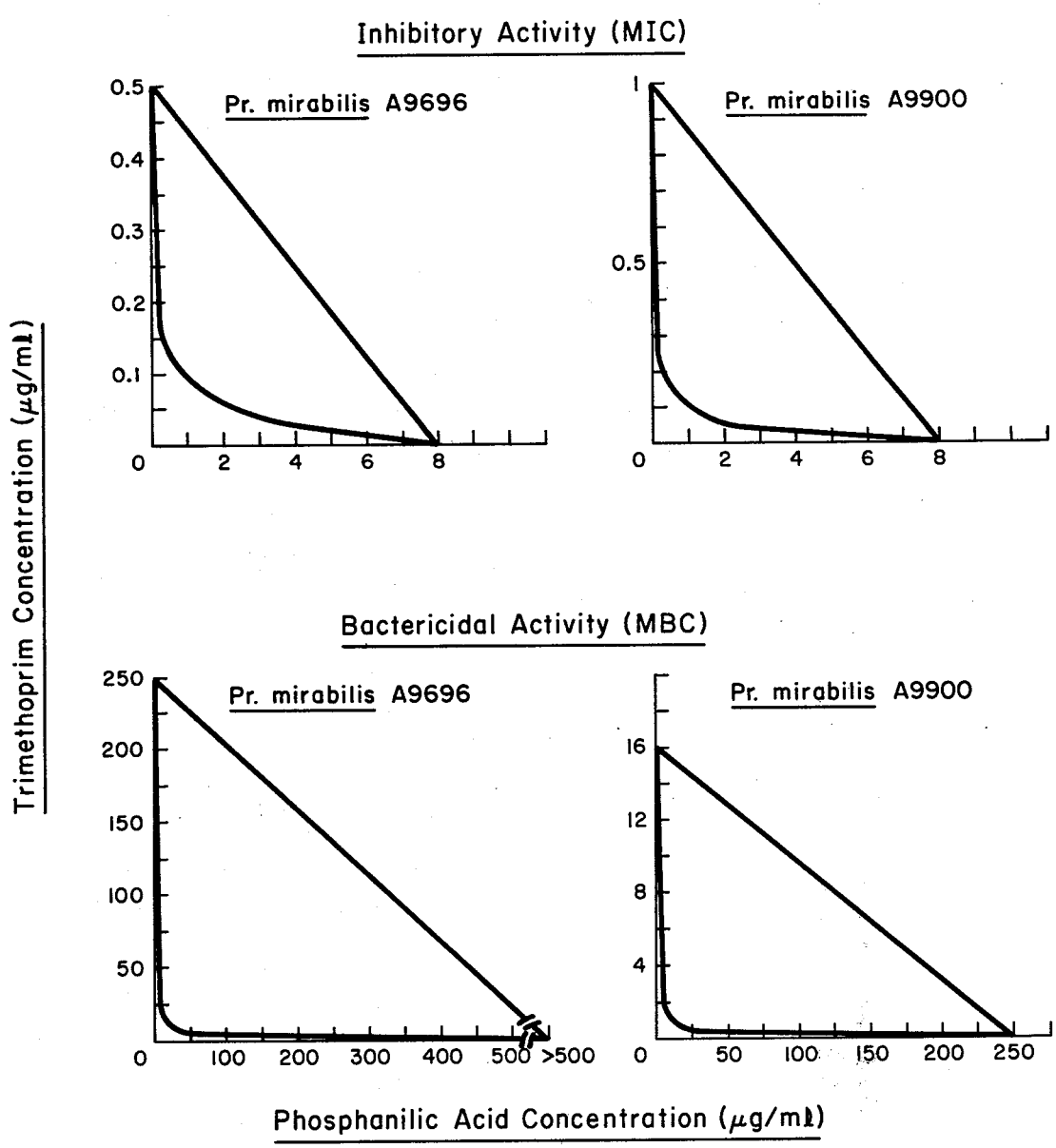
FIG. 1 contains four isobolograms which demonstrate the synergistic antibacterial activity (both inhibitory and bactericidal) of mixtures of phosphanilic acid and trimethoprim against two strains of Pr. mirabilis.
Figure 2:
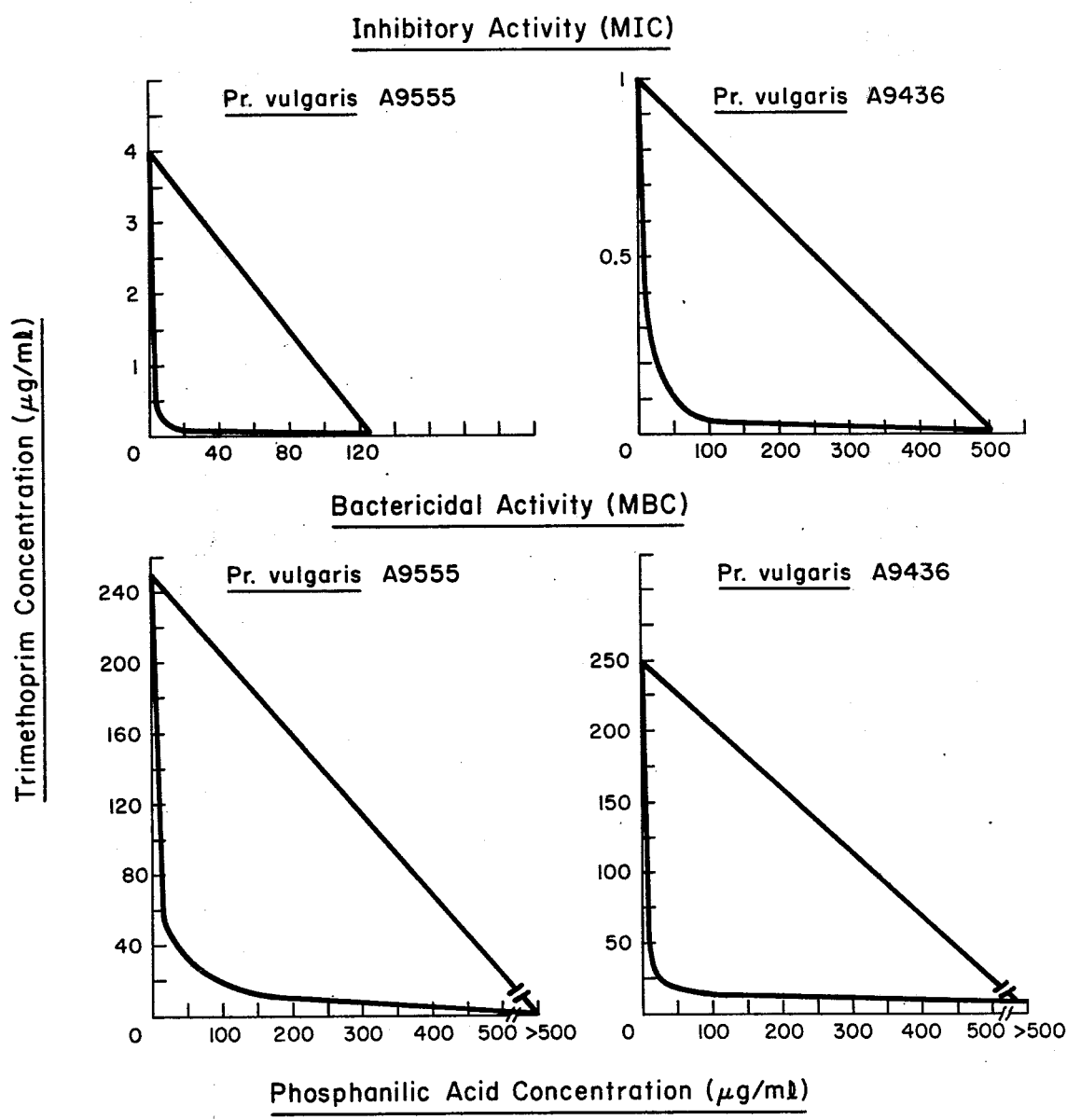
FIG. 2 contains four isobolograms which demonstrate the synergistic antibacterial activity (both inhibitory and bactericidal) of mixtures of phosphanilic acid and trimethoprim against two strains of Pr. vulgaris.
Figure 3:
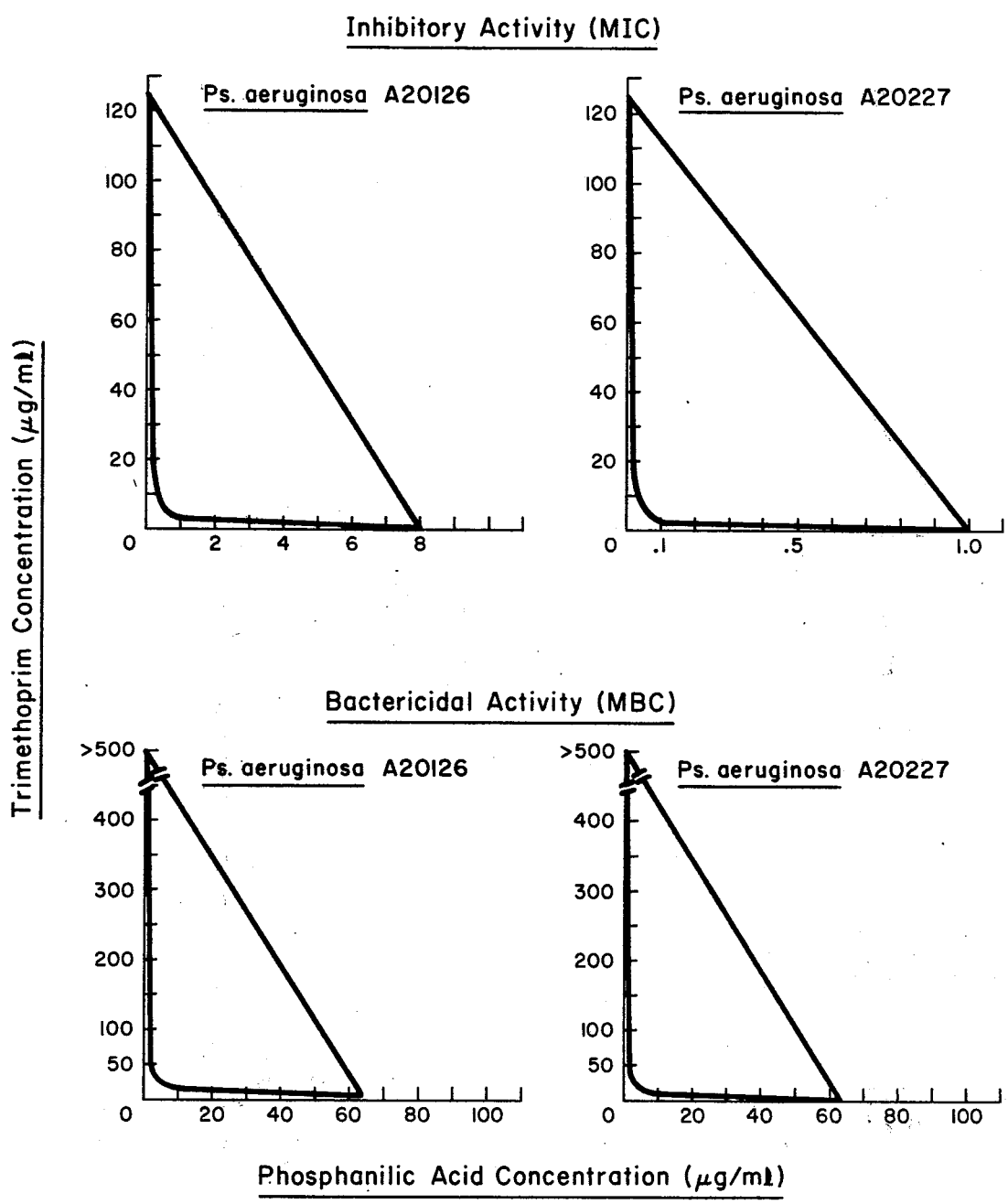
FIG. 3 contains four isobolograms which demonstrate the synergistic antibacterial activity (both inhibitory and bactericidal) of mixtures of phosphanilic acid and trimethoprim against two strains of Ps. aeruginosa.
Figure 4:
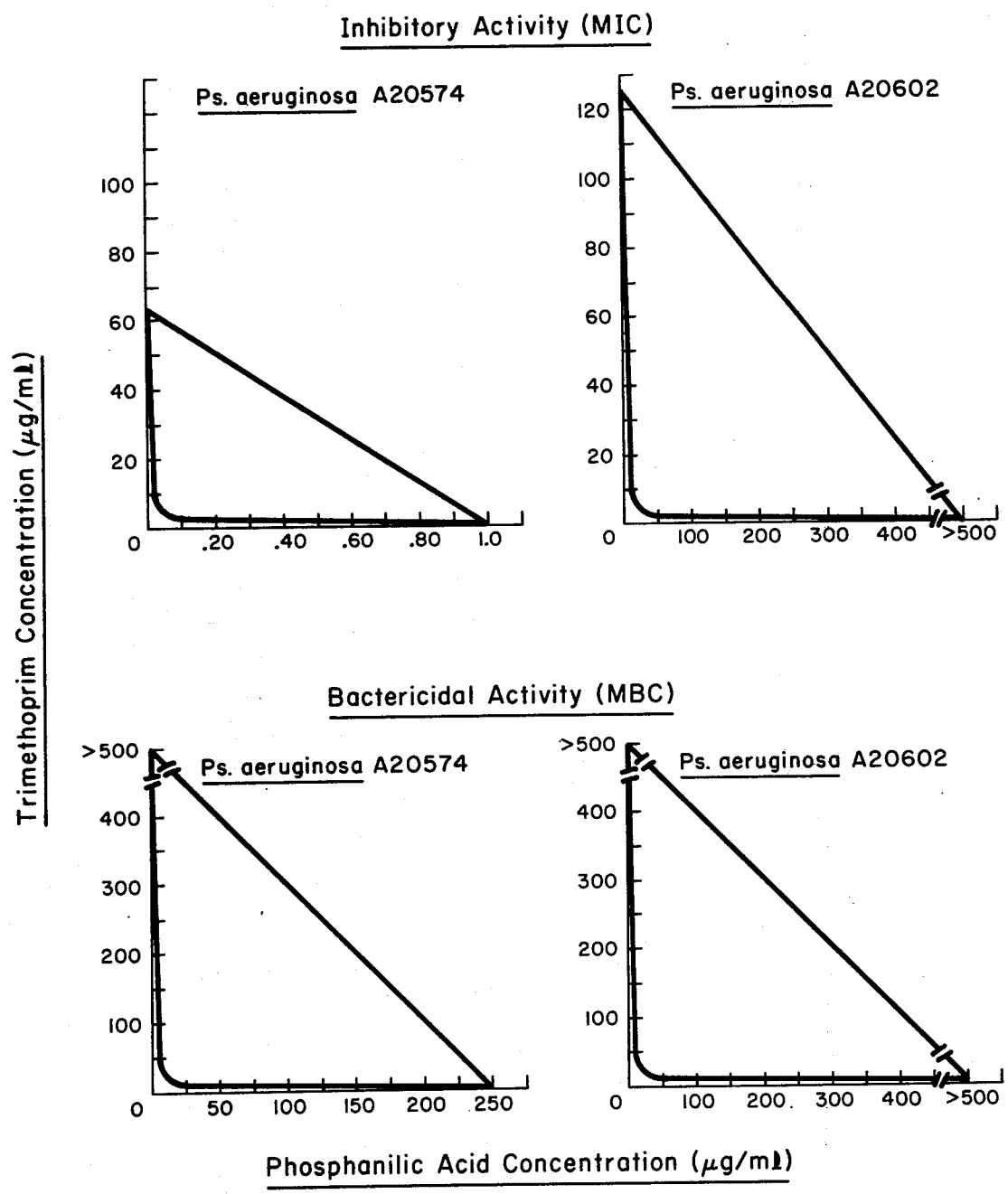
FIG. 4 contains four isobolograms which demonstrate the synergistic antibacterial activity (both inhibitory and bactericidal) of mixtures of phosphanilic acid and trimethoprim against two additional strains of Ps. aeruginosa.

The invention will be better understood by reference to the following examples which are given for illustrative purposes and are not meant to limit the invention.

EXAMPLE 1

Phosphanilic acid (4000 gms) and trimethoprim (800 gms) are intimately admixed and filled into 10,000 interlocking hard gelatin capsules, each containing 400 mg of phosphanilic acid and 80 mg of trimethoprim.

EXAMPLE 2

The general procedure of Example 1 is repeated except that the resulting mixture is filled into 5,000 interlocking capsules, each containing 800 mg of phosphanilic acid and 160 mg of trimethoprim.

EXAMPLE 3

| Capsule formulation: | Per capsule, mg. |
|---|---|
| phosphanilic acid | 400 |
| trimethoprim | 80 |
| lactose | 45 |
| cornstarch | 40 |
| magnesium stearate | 5 |
| Total | 570 |

Preparation: 400 parts of phosphanilic acid, 80 parts of trimethoprim, 45 parts of lactose, 40 parts of cornstarch and 5 parts of magnesium stearate are thoroughly blended, and the mixture is filled into suitably sized hard gelatin capsules to an approximate fill weight of 570 mg.

EXAMPLE 4

| Tablet formulation | Per tablet, mg. |
|---|---|
| phosphanilic acid | 800 |
| trimethoprim | 160 |
| cornstarch | 35 |
| lactose | 90 |
| gelatin | 12 |
| talcum | 16 |
| magnesium stearate | 7 |
| Total | 1120 |

Preparation: 800 parts of phosphanilic acid, 160 parts of trimethoprim 35 parts of cornstarch and 90 parts of lactose are thoroughly mixed in suitable blending equipment and granulated with an aqueous solution containing 12 parts of gelatin. The moist material is passed through a No. 12 screen and the granules are dried overnight on paper-lined trays. The dried granules are passed through a No. 14 screen and placed in a suitable mixer. Thereafter, 16 parts of talcum and 7 parts of magnesium stearate are added and the mixture is blended. The granulation is then compressed into tablets weighing approximately 1120 mg each, using flat, beveled edge, scored punches having a diameter of ½ inch.

EXAMPLE 5

| Tablet formulation: | Per tablet, mg |
|---|---|
| phosphanilic acid | 400 |
| trimethoprim | 80 |
| lactose | 95 |
| cornstarch-U.S.P. | 100 |
| prehydrolyzed cornstarch | 105 |
| talcum | 15 |

| Tablet formulation: | Per tablet, mg |
|---|---|
| magnesium stearate | 5 |
| Total | 800 |

Preparation: 400 parts of phosphanilic acid, 80 parts of trimethoprim, 95 parts of lactose, 100 parts of cornstarch-U.S.P. and 105 parts of prehydrolyzed cornstarch are placed in a suitable mixer and blended until uniform. The blended powders are passed through a Model D Fitzmill at high speed with hammers forward using a No. 00 screen. This premix is transferred to a suitable blender. The blended powders are granulated with distilled water and the wet granulation is passed through a Model D Fitzmill with knives forward at slow speed using a No. 4B screen. The milled, wet granules are dried and the dry granules are passed through a Model D Fitzmill at medium speed with knives forward using a No. 12 screen. The milled, dry granulation is transferred to a suitable blender and 15 parts of talcum and 5 parts of magnesium stearate are added and mixed until uniform. The granulation is compressed into tablets weighing approximately 800 mg each, using flat, beveled edge, scored punches having a diameter of 15/32 inch.

I claim:

1. An orally active antibacterial composition comprising from about 0.25 to about 20 parts of phosphanilic acid or a pharmaceutically acceptable salt thereof and one part of trimethoprim or a pharmaceutically acceptable salt thereof.

2. A composition according to claim 1 comprising from about 2 to about 7 parts of phosphanilic acid or a pharmaceutically acceptable salt thereof and one part of trimethoprim or a pharmaceutically acceptable salt thereof.

3. A composition according to claim 1 comprising about 5 parts of phosphanilic acid or a pharmaceutically acceptable salt thereof and one part of trimethoprim or a pharmaceutically acceptable salt thereof.

4. An antibacterial composition for oral administration in shaped dosage unit form comprising from about 100 to about 1600 milligrams of phosphanilic acid or a pharmaceutically acceptable salt thereof and from about 20 to about 320 milligrams of trimethoprim or a pharmaceutically acceptable salt thereof.

5. An antibacterial composition according to claim 4 comprising from about 400 to about 800 milligrams of phosphanilic acid or a pharmaceutically acceptable salt thereof and from about 80 to about 160 milligrams of trimethoprim or a pharmaceutically acceptable salt thereof.

6. A method of treating a warm-blooded animal afflicted with a bacterial disease which comprises orally administering to said warm-blooded animal an antibacterially effective amount of a composition comprising from about 0.25 to about 20 parts of phosphanilic acid or a pharmaceutically acceptable salt thereof and one part of trimethoprim or a pharmaceutically acceptable salt thereof.

7. A method in accordance with claim 6 wherein the composition comprises from about 2 to about 7 parts of phosphanilic acid or a pharmaceutically acceptable salt thereof and one part of trimethoprim or a pharmaceutically acceptable salt thereof.

8. A method in accordance with claim 6 wherein the antibacterially effective amount of the composition comprises from about 100 to about 1600 milligrams of phosphanilic acid or a pharmaceutically acceptable salt thereof and from about 20 to about 320 milligrams of trimethoprim or a pharmaceutically acceptable salt thereof.

9. A method in accordance with claim 6 wherein the antibacterially effective amount of the composition comprises from about 400 to about 800 milligrams of phosphanilic acid or a pharmaceutically acceptable salt thereof and from about 80 to about 160 milligrams of trimethoprim or a pharmaceutically acceptable salt thereof.

* * * * *